(12) United States Patent
Isozaki et al.

(10) Patent No.: US 6,204,918 B1
(45) Date of Patent: Mar. 20, 2001

(54) APPARATUS FOR SURFACE INSPECTION

(75) Inventors: Hisashi Isozaki; Yutaka Shida; Takuji Sato, all of Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 09/285,259

(22) Filed: Apr. 2, 1999

(30) Foreign Application Priority Data

Apr. 13, 1998 (JP) ................................................. 10-115884

(51) Int. Cl.$^7$ .................................................. G01N 21/00
(52) U.S. Cl. ...................................... 356/239.8; 356/237.4
(58) Field of Search ............................... 356/237.1, 239.1, 356/239.2, 239.3, 239.7, 239.8, 237.2, 237.3, 237.4, 237.5, 394, 388, 398, 431; 250/358.1, 360.1, 559.01, 559.16, 559.18

(56) References Cited

U.S. PATENT DOCUMENTS

| | | | |
|---|---|---|---|
| 4,641,967 | * | 2/1987 | Pecen ................................... 356/237 |
| 5,461,474 | * | 10/1995 | Yoshii et al. ......................... 356/237 |
| 5,625,193 | * | 4/1997 | Broude et al. ....................... 250/372 |

* cited by examiner

*Primary Examiner*—Frank G. Font
*Assistant Examiner*—Michael P. Stafira
(74) *Attorney, Agent, or Firm*—Foley & Lardner

(57) ABSTRACT

An apparatus for surface inspection according to the invention comprises an irradiating optical system for throwing an irradiating light beam from a light source onto the surface of an object of inspection, a light receiving optical system for receiving a scattered light beam reflected from the surface of the object of inspection irradiated by the irradiating optical system, a photosensing portion for forming a surface data signal from the scattered light beam received by the light receiving optical system, a displacement portion for displacing the surface of the object of inspection relative to the irradiating optical system, plus the light receiving optical system, continuously in the main scanning direction and intermittently in the sub-scanning direction, and a foreign matter detecting portion for detecting a foreign matter present on the surface of the object of inspection on the basis of the maximum value level of the surface data signal and obtaining the position, in the sub-scanning direction, of the foreign matter present on the surface of the object of inspection on the basis of at least two adjoining surface data signals in the sub-scanning direction.

10 Claims, 17 Drawing Sheets

APPARATUS FOR SURFACE INSPECTION

TECHNICAL FIELD

The present invention relates to a surface inspecting apparatus for measuring precisely the position of a foreign matter present on a surface.

PRIOR ART

Of conventional surface inspecting apparatuses, those are known in which the surface of an object of inspection is subjected to a spiral scan or a linear luster scan with the use of an irradiating light beam and a foreign matter present on the reflecting surface is detected according to the level of received-light signals derived from reflected light beams from the surface.

In the prior art apparatuses, when the direction in which a light beam is continuously moved is called the main scanning direction and the direction in which the light beam is intermittently moved is called the sub-scanning direction, it becomes necessary to make the pitch of movement of the beam finer in the sub-scanning direction if it is desired that the position of the object of inspection in the sub-scanning direction be measured with high resolution.

However, when the pitch of movement in the sub-scanning direction is made finer, such a difficulty arises that the tact time is prolonged and the time required for measurement becomes longer.

SUMMARY OF THE INVENTION

An object of the invention is to provide a surface inspecting apparatus capable of measuring the position, in the sub-scanning direction, of a foreign matter, as the object of inspection, with high resolution without making finer the pitch of movement of the beam in the sub-scanning direction and prolonging the tact time.

A surface inspecting apparatus according to the invention is a surface inspecting apparatus capable of accurately measuring the position of a foreign matter (a comprehensive term embracing a dust, flaw, particle and the like) present on the surface of such a material as a semiconductor wafer.

A surface inspecting apparatus of the invention comprises, for example, a light source, an irradiating optical system for throwing an irradiating light beam from the light source onto the surface of an object of inspection, a light receiving optical system for receiving a scattered light beam reflected from the surface of the object of inspection irradiated by the irradiating optical system, a photosensing portion for forming a surface data signal from the scattered light beam received by the light receiving optical system, a displacement portion for providing the surface of the object of inspection and the irradiating optical system, plus the light receiving optical system, with displacement relative to each other, continuously in the main scanning direction and intermittently in the sub-scanning direction, and a foreign matter detecting portion for detecting a foreign matter present on the surface of the object of inspection on the basis of the maximum level of the surface data signal and obtaining the position, in the sub-scanning direction, of the foreign matter present on the surface of the object of inspection on the basis of at least two adjoining surface data signals in the sub-scanning direction.

Preferably, the foreign matter detecting portion is adapted to obtain the position of a foreign matter present on the surface of the object of inspection on the basis of the levels of at least two adjoining surface data signals in the sub-scanning direction.

Further, the foreign matter detecting portion is adapted to obtain the position, in the main scanning direction and the sub-scanning direction, of the foreign matter present on the surface of the object of inspection on the basis of the levels of at least two adjoining surface data signals in the sub-scanning direction on the presumption that the intensity distribution of the irradiating light beam of the irradiating optical system is in conformity with a specific curve.

Further, the foreign matter detecting portion is adapted to obtain the position, in the sub-scanning direction, of the foreign matter present on the surface of the object of inspection on the basis of the levels of at least two adjoining surface data signals in the sub-scanning direction on the presumption that the intensity distribution of the irradiating light beam of the irradiating optical system is in conformity with a Gaussian curve, according to Formula 1 as mentioned below:

$$x = \{(D^2/8)\ln(I1/I2) - p^2\}/2p \quad \text{Formula 1}$$

In Formula 1, D is the beam diameter, p is the scanning pitch, n is the scanning number of the beam, In is the peak level of the n-th received-light signal, and In+1 is the peak level of the (n+1)-th received-light signal.

In a preferred embodiment of the invention, the foreign matter detecting portion is adapted to obtain the position, in the main scanning direction and the sub-scanning direction, of the center of the foreign matter present on the surface of the object of inspection on the basis of positional data of at least two adjoining surface data signals in the sub-scanning direction.

Further, the foreign matter detecting portion is adapted to obtain the position, in the main scanning direction and the sub-scanning direction, of the foreign matter present on the surface of the object of inspection by obtaining the position of the center of gravity of the object of inspection from the starting position and the ending positions of at least two adjoining surface data signals in the sub-scanning direction.

Further, the foreign matter detecting portion is adapted to obtain the position, in the main scanning direction and the sub-scanning direction, of the center of the foreign matter present on the surface of the object of inspection on the basis of a change in the surface data signal in the main scanning direction.

Further, the foreign matter detecting portion is adapted to obtain a sectional area caused by the foreign matter from changes in the main scanning direction of the surface data signals of adjoining surface data signals and, thereupon, to obtain the position, in the main scanning direction and the sub-scanning direction, of the center of the foreign matter present on the surface of the object of inspection on the basis of the obtained sectional area.

Description will be made taking a surface inspecting apparatus of a semiconductor wafer as an example. In measuring a foreign matter, such as a dust, a flaw, or the like, present on the surface of the semiconductor, there are various ways of beam scanning. In any of these beam scanning methods, the point where the scattered light beam by a foreign matter exceeds a threshold is stored as a Start, the point where the light beam falls below the threshold is recorded as an End, and a Peak of the scattered light beam by the foreign matter is recorded between the Start and the End, and these Start, End, and Peak are treated as data of one foreign matter. For example, a scattered light beam by a foreign matter is detected by an A/D sensor with a high resolving power and the point where the beam exceeds a threshold is stored as a Start, a Peak of the scattered light beam by the foreign matter is recorded, and the point where the beam falls below the threshold is recorded as an End, and these are treated as data of one foreign matter.

Preferably, an A/D clock counter may be used to record the accurate coordinate of each point (Start, Peak, and End) as data. As additional data, the coordinate of the scanning direction and the current scanning number are stored.

When data of one foreign matter are detected at two or more times of scanning, a Gaussian correction (to be described later in detail) is made by utilizing the peak data (the maximum values of the data) in the scanning and, thereupon, an ideal peak position of the foreign matter is obtained by calculation. The thus obtained coordinate of the peak position is recorded as the real coordinate of the foreign matter. And, the value of the data at the obtained peak position is recorded as the real peak data of the foreign matter.

Another method is like this. When data of one foreign matter are detected in two or more times of scanning, the position of the center of gravity of the area formed between the Start and the End of the foreign matter data is obtained and this point is defined as the real coordinate position of the foreign matter.

Still another method is as follows. When data of one foreign matter are detected in two or more times of scanning, a Gaussian correction is made by utilizing the positional data of the Start, the End, and the Peak of the data of the foreign matter and, thereby, two-dimensional sectional areas are calculated. The sectional area in each scan is obtained and, using the shapes of the sectional areas, a further Gaussian correction is carried out three-dimensionally and the real coordinate of the center is obtained. Namely, Gaussian corrections are made in both the direction in which the beam is continuously moved (main scanning direction) and the direction in which the beam is moved intermittently (sub-scanning direction). The data at the obtained real coordinate is recorded as a Peak.

By performing the processes as described above, even if the beam is scanned at a coarse scanning pitch (scanning distance) in the direction in which the beam is intermittently moved (sub-scanning direction), it becomes possible to improve the precision in the detection of the coordinate of the foreign matter. Further, since the real peak data can be calculated, the shape of the scanning beam can be corrected and, thereby, the same result as obtained in scanning with the same light power can be obtained and the fluctuations in the scattered light beam caused by the foreign matter can be suppressed. Consequently, more accurate foreign matter inspection can be achieved.

Further, if the beam shape gone through a Gaussian correction as described above and mechanical precision can be obtained, a highly accurate position coordinate and peak data can be obtained even from data provided by scanning at a coarse pitch.

Description on Gaussian corrections will be made as follows:

(A) First, a Gaussian correction of the peak data in the scanning direction (main scanning direction) will be described.

1. When more than one set of data (Start, Peak, End, and the scanning number) are obtained by scanning at a coarse pitch, a Gaussian fit is applied to the peak data (including the coordinate) in each scanning position.

2. If a Gaussian curve connecting the peaks of the more than one set of data is obtained, the position coordinate of the peak of the curve and the peak data can be obtained.

3. The data are defined as the real coordinate of the foreign matter and the peak data.

(B) Next, a method of obtaining data from the area formed between a Start and an End will be described.

1. When more than one set of data (Start, Peak, End, and the scanning number) are obtained by scanning at a coarse pitch, the area formed between the Start and the End in each scanning position is obtained.

2. The center of gravity of each area is obtained.

3. The position of the center of gravity is defined as the real coordinate of the foreign matter.

(C) A method of obtaining data from the Gaussian sectional area in each scan will be described.

1. A Gaussian fit is applied by using data (Start, Peak, and End) obtained in each scan.

2. When there are more than one set of scan data, the sectional area caused by the foreign matter in each scan can be obtained.

3. A three-dimensional Gaussian fit is applied by using the sectional areas and thereby the real coordinate and the peak data are obtained.

4. The data are defined as the real coordinate of the foreign matter and the peak data.

The following effects can be obtained from the invention.

A coordinate can be obtained with sufficiently high precision even with a coarse scan pitch. Results equivalent to those obtained by uniform power can be obtained irrespective of the shape of the scanning light beam and, thereby, fluctuations in data can be decreased.

DESCRIPTION OF THE PREFERRED EMBODIMENTS

A Gaussian correction method of the peak data in the scanning direction (main scanning direction) will be described with reference to FIG. 1.

Figure 20:
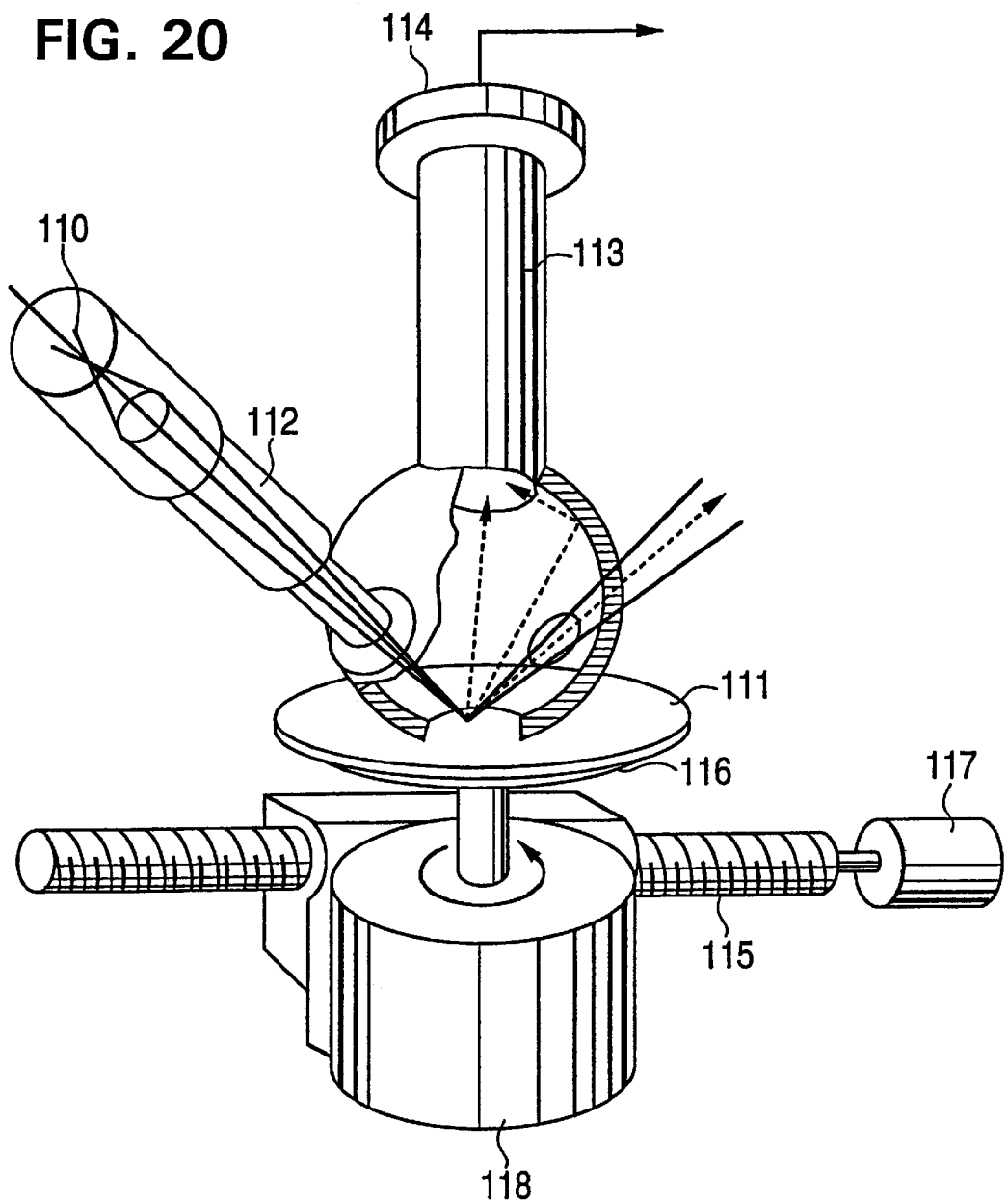
FIG. 20 is a perspective view of a surface inspection arrangement which is used in connection with the embodiments of the invention for carrying out the disclosed surface inspection.

The apparatus as shown in FIG. 20, comprises a light source 110, an irradiating optical system 112 for projecting a light beam from the light source 110 on the surface of the object under measurement 111, a light receiving optical system 113 receiving a scattered light beam reflected from the surface of the object under measurement 111 irradiated by the irradiating optical system 112 for forming a received-light signal, a photoelectric converting element 114 for outputting the received light by the light receiving optical system 113 as a sensed-light signal, and a linear displacement portion 115 for providing the surface of the object under inspection 111 and the irradiating optical system 112, plus the light receiving system 113, with linear relative displacement, as well as a rotational displacement portion 116 for providing the surface of the object under inspection 111 and the irradiating optical system 112, plus the light receiving system 113, with rotational relative displacement, whereby the irradiating light beam is induced to perform a spiral scan of the surface of the object under inspection 111. The linear displacement portion 115 and the rotational displacement portion 116 are coupled with motors 117 and 118, respectively.

Figure 1A:
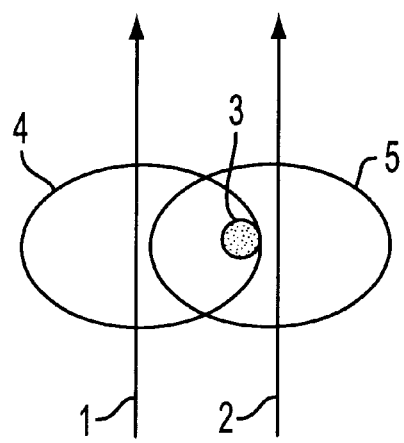
FIGS. 1(A), (B), and (C) are explanatory drawings of a concept of the processing procedure according to the invention.

Referring to FIG. 1, a laser beam is continuously moved in the main scanning direction. Further, the laser beam is intermittently moved in the sub-scanning direction. As the scanning methods, there are one method, in which a wafer is rotated, while a laser beam is impinged thereon, such that the relative position between the rotating wafer and the laser beam is changed and a laser beam is allowed to spirally scan the surface of a wafer and the other method, in which main scanning is made by linearly moving a laser beam with respect to a wafer and sub-scanning is made by intermittently moving the laser beam with respect to the wafer in the direction perpendicular to the main scanning direction (in the sub-scanning direction) and the laser beam is allowed to linearly scan the surface of the wafer. As an example of the spiral scanning, Japanese Patent Application No. 9-345736 can be mentioned. As shown in FIG. 1(A), for example, the laser beam 4 is continuously scanned on the wafer surface in the direction of the arrow 1 (main scanning direction) and then the laser beam 5 is continuously scanned in the direction of the arrow 2 (main scanning direction). If at this time there is a foreign matter 3 present on the surface of the wafer, scattered light beams by the foreign matter 3 in both of the scanning steps with the laser beams 4 and 5 are sensed by an A/D sensor with a high resolving power. When data of one foreign matter 3 are thus detected in two or more times of scanning, Gaussian correction is applied to the data.

Figures 1B, 1C:
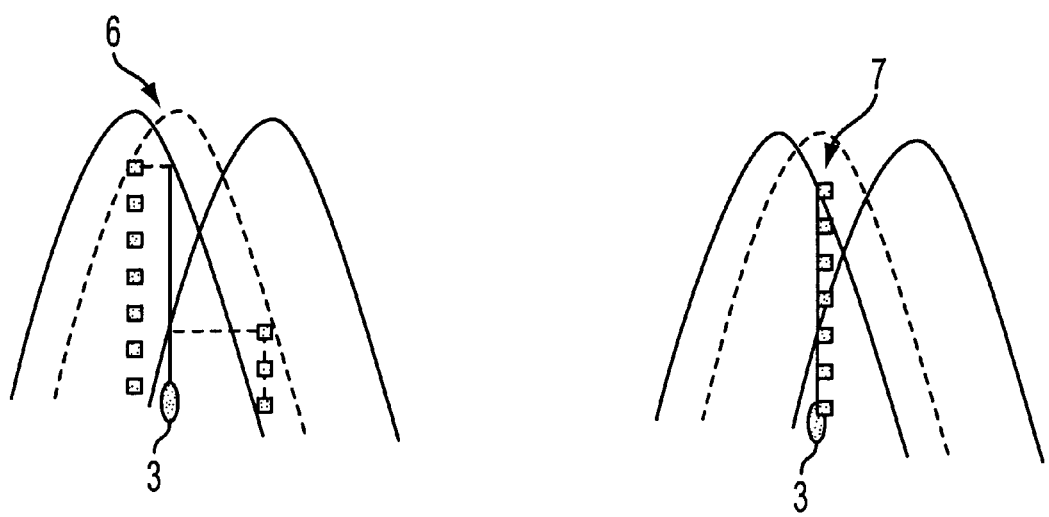

When more than one set of data (Start, Peak, End, and the scanning number) are obtained by scanning at a coarse pitch, a Gaussian fit is applied to the peak data (including coordinate) in each scanning position and a Gaussian curve 6 connecting the peaks of the more than one set of data is obtained as indicated the fine broken line in FIG. 1(B) and, then, the peak position coordinate and the peak data of the curve 6 are obtained as indicated by the thick broken line 7 in FIG. 1(C). Then, the data are defined as the real coordinate and the peak data of the foreign matter.

Now, the relationship between measured values of two points of the Gaussian beam and the peak position will be described in concrete terms.

Figure 12:
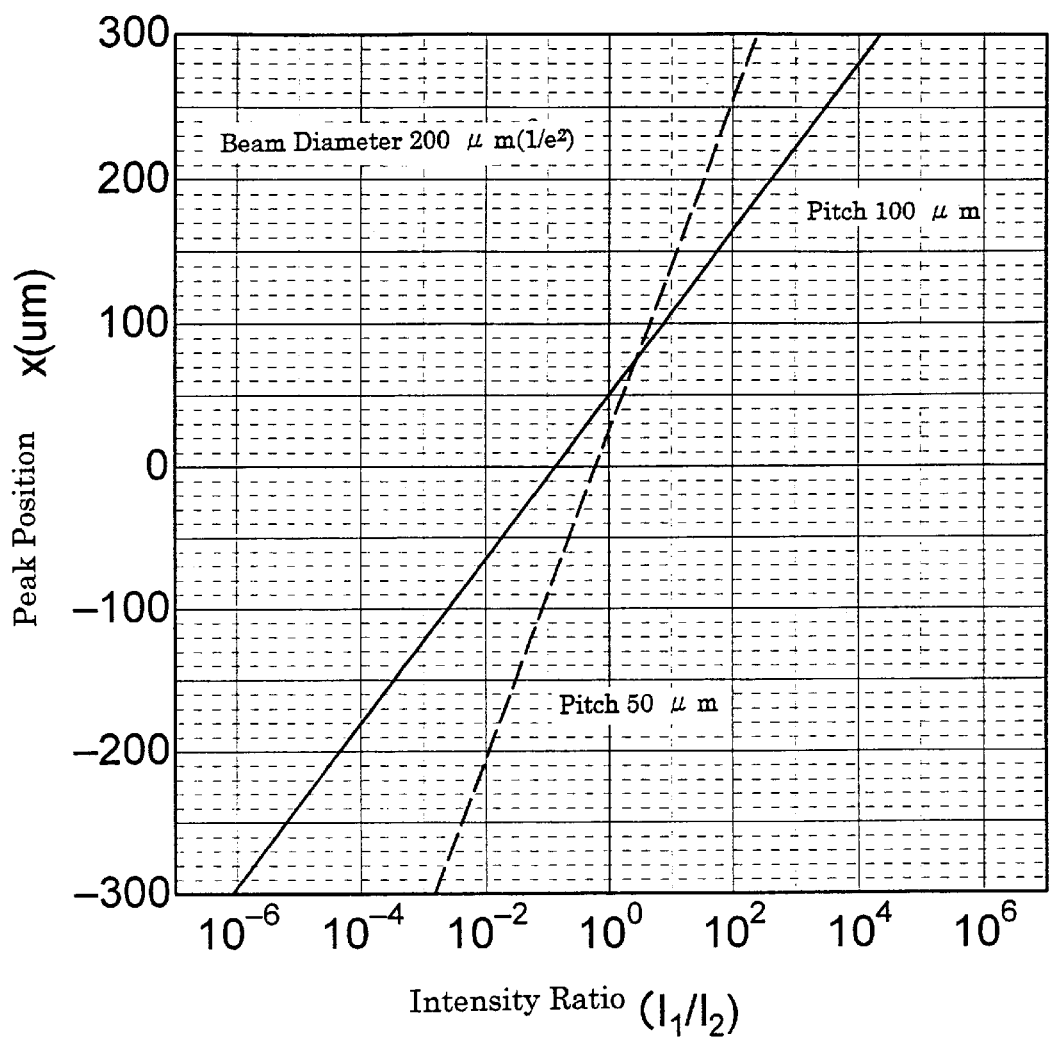
FIG. 12 is a graph showing an example of the relationship between the peak value and the intensity ratio of a Gaussian beam used in the surface inspecting apparatus of the invention.

FIG. 12 shows the relationship between the peak value and the intensity ratio in a Gaussian beam with the beam diameter of 200 μm. The solid line indicates the case where the pitch is 100 μm and the broken line indicates the case where the pitch is 50 μm.

In a surface inspecting apparatus scanning the surface of a wafer with a laser beam, of which the center intensity is $L_0$ and the beam diameter is $D(1/e^2)$, when the detected light quantity from a particle (foreign matter) became $I_1$ at the time of the first scan and $I_2$ at the time of the next scan which was made at the position intermittently shifted a pitch p in the sub-scanning direction, the distance x from the center beam at the time of the first scan to the position of the particle will be calculated.

The product of the coefficient of scattering from the particle and the detecting efficiency is represented by a and the radius of the beam (D/2) by r.

$$I_1 = aL_0 \exp\left(\frac{-2x^2}{r^2}\right) \qquad \text{Formula 2}$$

$$I_2 = aL_0 \exp\left(\frac{-2(x+p)^2}{r^2}\right)$$

$$\frac{I_1}{I_2} = \frac{\exp\left(\frac{-2x^2}{r^2}\right)}{\exp\left(\frac{-2(x+p)^2}{r^2}\right)} = \exp\left[\frac{+2}{r^2}(p^2 + 2px)\right]$$

$$\ln\left(\frac{I_1}{I_2}\right) = \frac{+2}{r^2}(p^2 + 2px)$$

Consequently, the center of the particle is expressed as $$x = \frac{\frac{r^2}{2}\ln\left(\frac{I_1}{I_2}\right) - p^2}{2p} = \frac{\frac{D^2}{8}\ln\left(\frac{I_1}{I_2}\right) - p^2}{2p} \qquad \text{Formula 3}$$

Further, the detected light quantity at the time when the center of the beam concurs with the center of the particle is expressed as $$I_0 = I_1 \exp\left(\frac{2x^2}{r^2}\right) \qquad \text{Formula 4}$$

Figure 13:
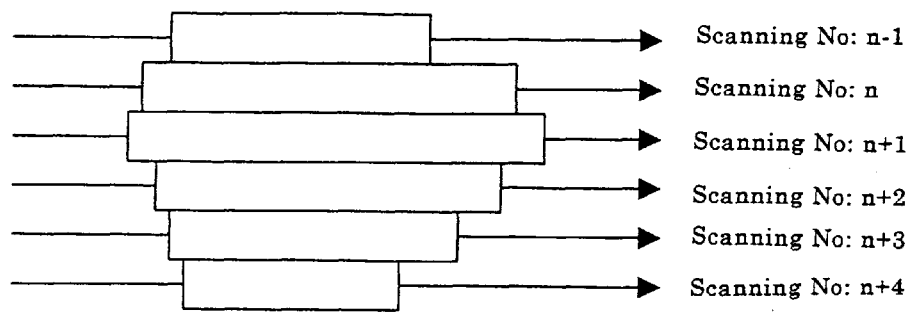
FIG. 13 is a diagram showing an example of the area formed between Starts and Ends of one foreign matter.
Figure 14:
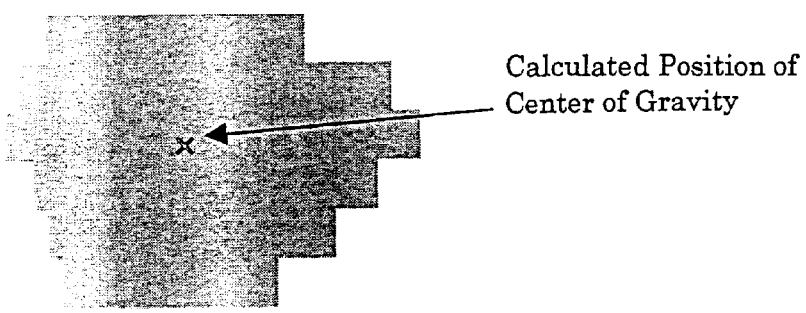
FIG. 14 is a diagram showing an example of the method of obtaining the center of gravity from an area formed between Starts and Ends of one foreign matter.

When three or more sets of peak data are used, a method to use the average value of the values obtained from combinations of two sets of these data or a statistical method such as least square approximation may be used. Referring to FIGS. 13 and 14, a method for obtaining the coordinate of a foreign matter from areas formed between Starts and Ends will be described.

When more than one set of data of the Start, Peak, End, and the scanning number are obtained as shown in FIG. 13 through scanning made in the main scanning direction (the horizontal direction in FIG. 13) at a coarse pitch (in the sub-scanning direction, i.e., the vertical direction in FIG. 13), the area formed between the Starts and the Ends in all the scanning positions (i.e., the total areas of the six rectangles in FIG. 13) is obtained.

The center of gravity (the position indicated by X) of the area is obtained as shown in FIG. 14. The position of the center of gravity is defined as the real coordinate of the foreign matter.

Figure 15:
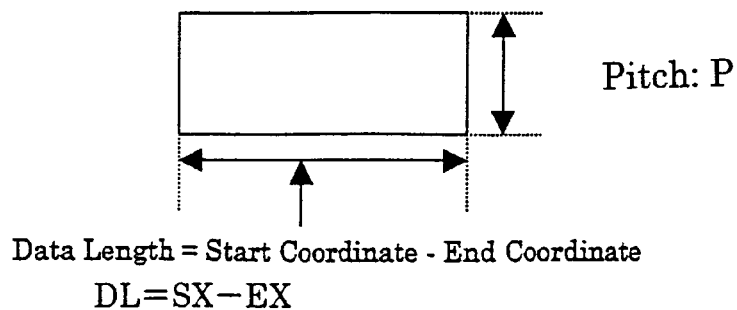
FIG. 15 is a diagram showing another example of the area formed between a Start and an End of one foreign matter.
Figure 16:
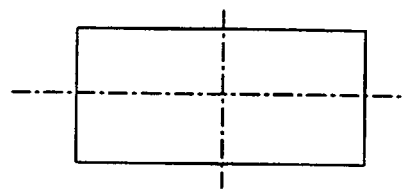
FIG. 16 is a diagram showing an example of the method of obtaining the center of gravity from the area shown in FIG. 15.
Figure 17:
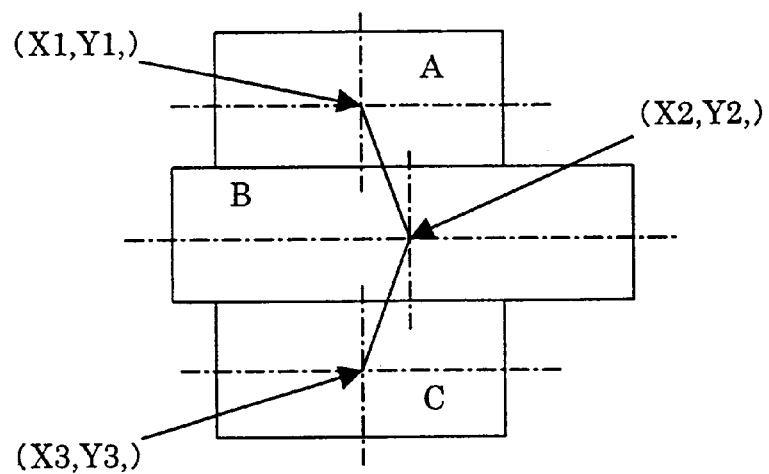
FIG. 17 is a diagram showing an example of the method of obtaining the center of gravity from the three points with the area and the center of gravity of FIG. 15 and FIG. 16 taken into consideration.

Referring now to FIGS. 15–17, a method obtaining the coordinate from the area without weighting will be described.

One each set of data is processed. For example, one set of scan data is obtained from information of the Start and the End as shown in FIG. 15.

The center of gravity of one area is simply given by the intersection of the lines connecting centers of the sides as shown in FIG. 16. Taking this into consideration, the model shown in FIG. 17 will be calculated.

Since there are three points in the case of this model, the center of gravity can be obtained from these expressions:

ABC(X)=(X1+X2+X3)/3

ABC(Y)=(Y1+Y2+Y3)/3

When the number of areas is larger than the above, i.e., four or more, the following Formulas can be used.

$$X = \frac{\sum_{i=1}^{n} Xi}{n} \quad Y = \frac{\sum_{i=1}^{n} Yi}{n} \qquad \text{Formula 5}$$

To improve the precision, it is also possible to make calculation with the coordinates weighted. For example, concerning the area and the peak data value, the area in each scan may be used as the weight or the peak data value may be used as the weight.

Figure 18:
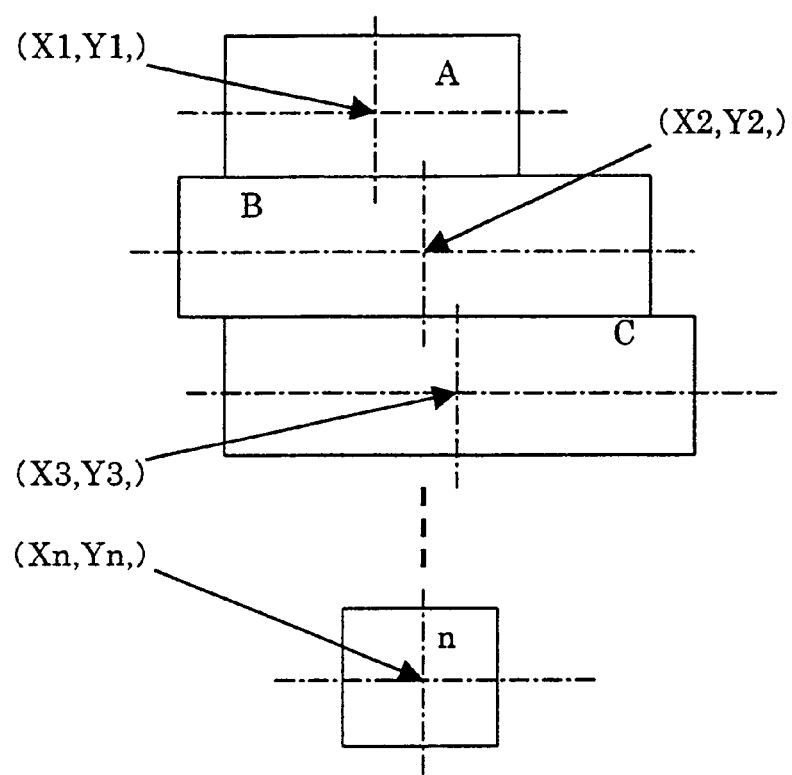
FIG. 18 is a diagram showing another example in which the coordinate is weighted by the area formed between a Start and an End of one foreign matter.

Considering here the weight to be K, the model shown in FIG. 18 will be taken up.

Denoting the respective weights by S1, S2, . . . , Sn, the coordinates can be obtained from the following Formulas.

$$X = \frac{1}{n} \times \sum_{i=1}^{n} Xi \times \frac{Si}{(S1+S2+\ldots+Sn)} \qquad \text{Formula 6}$$

$$Y = \frac{1}{n} \times \sum_{i=1}^{n} Yi \times \frac{Si}{(S1+S2+\ldots+Sn)}$$

Figure 19:
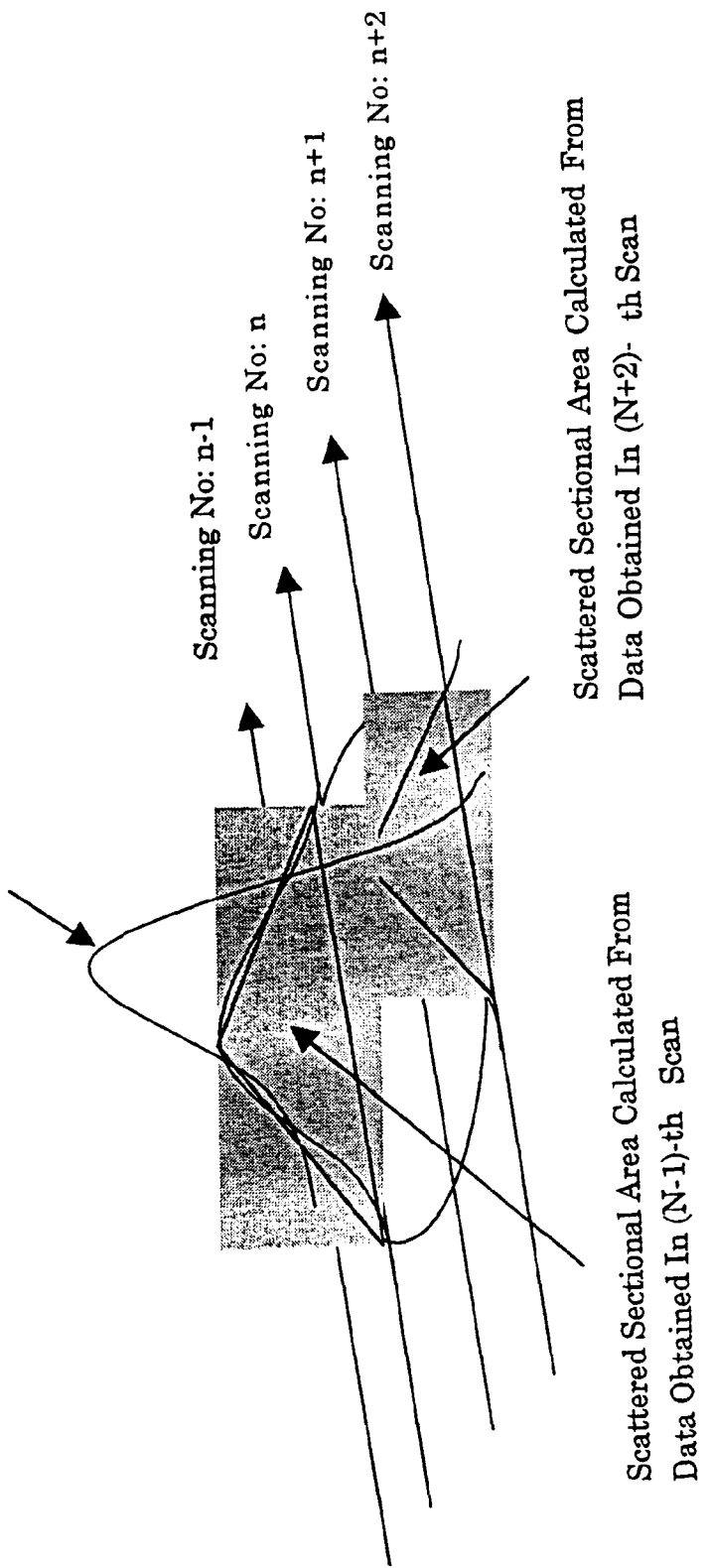
FIG. 19 is a diagram showing a scattered contour inferred from the Gaussian sectional area in each scan.

Referring to FIG. 19, a method in which the data are obtained from the Gaussian sectional area in each of the scan positions will be described.

1) The Gaussian fit is applied by using the data (Start, Peak, and End) obtained in each scanning position.

2) When there are more than one set of scan data, the sectional area from the foreign matter in each scan can be obtained.

3) By using the sectional areas, a Gaussian fit is applied in a three-dimensional manner and, thereby, the real coordinate and peak data are obtained.

4) These data are defined as the real coordinate and the peak data of the foreign matter.

Next, the threshold level position of the Gaussian beam and the center of the beam will be described concretely.

Generally, a Gaussian beam whose section is an ellipse is used. The beam, with the center of the beam in the center of the coordinate system, is expressed as:

$$L_0 \exp\left(\frac{-2x^2}{r_x^2}\right) \exp\left(\frac{-2y^2}{r_y^2}\right) = L_0 \exp\left\{-2\left(\frac{x^2}{r_x^2} + \frac{y^2}{r_y^2}\right)\right\} \qquad \text{Formula 7}$$

where $L_0$ is the intensity in the center, $r_x$ is the $e^{-2}$ radius of the beam in the direction x and $r_y$ is the $e^{-2}$ radius of the beam in the direction y.

When the product of the scattering coefficient of a particle (foreign matter) and the light receiving efficiency is denoted by a, the received light intensity I is expressed as:

$$I = aL_0 \exp\left\{-2\left(\frac{x^2}{r_x^2} + \frac{y^2}{r_y^2}\right)\right\} \qquad \text{Formula 8}$$

An edge at a threshold level Is has the coordinate satisfying the following Formula.

$$I_s = aL_0 \exp\left\{-2\left(\frac{x^2}{r_x^2} + \frac{y^2}{r_y^2}\right)\right\} \qquad \text{Formula 9}$$

By transforming this Formula, Formulas 10, 11, and 12 can be obtained.

$$\frac{-1}{2}\ln\left(\frac{I_s}{aL_0}\right) = \frac{x^2}{r_x^2} + \frac{y^2}{r_y^2} \qquad \text{Formula 10}$$

$$k = \frac{1}{\sqrt{\frac{-1}{2}\ln\left(\frac{I_s}{aL_0}\right)}} \qquad \text{Formula 11}$$

$$1 = \frac{x^2}{(kr_x)^2} + \frac{y^2}{(kr_y)^2} \qquad \text{Formula 12}$$

From this, it is known that the section becomes an ellipse having radii $kr_x$ and $kr_y$.

Further, supposing that coordinates (x1, y1) and (x2, y1+p) at the threshold value Is could be measured, the following Formulas 13 and 14 can be derived from Formula 10.

$$\frac{x_1^2}{r_x^2} + \frac{y_1^2}{r_y^2} = \frac{x_2^2}{r_x^2} + \frac{(y_1+p)^2}{r_y^2} \qquad \text{Formula 13}$$

$$y_1 = \frac{\frac{x_1^2 - x_2^2}{r_x^2} - \frac{p^2}{r_y^2}}{2p} \qquad \text{Formula 14}$$

In reality, when half the distance between the start and the end in the first scan is represented by $x_1$ and half the distance between the start and the end in the scan a pitch p apart from the first scan is represented by $x_2$, the center of the particle is located at a position a distance $y_1$ apart from the center of the first scan in the sub-scanning direction.

The signal intensity $I_0$ in the center is expressed as:

$$I_o = aL_o \quad \text{Formula 15}$$

By substituting this Formula into Formula 9 and making transformation, the following Formula can be obtained:

$$I_0 = I_s \exp\left\{2\left(\frac{x_1^2}{r_x^2} + \frac{y_1^2}{r_y^2}\right)\right\} \quad \text{Formula 16}$$

By substituting $x_1$ and $y_1$, which is obtained above, we can obtain the center signal intensity.

From Formula 12, the area S of the ellipse at the threshold level plane can be obtained as follows:

$$S = \pi k^2 r_x r_y \quad \text{Formula 17}$$

By having the area S obtained at the time of calculation of the center of gravity in the center-of-gravity method, the center intensity can be obtained by the following expression:

$$I_0 = I_s \exp\left(\frac{2\pi r_x r_y}{S}\right) \quad \text{Formula 18}$$

EMBODIMENT SHOWN IN FIGS. 2–5

Figure 2:
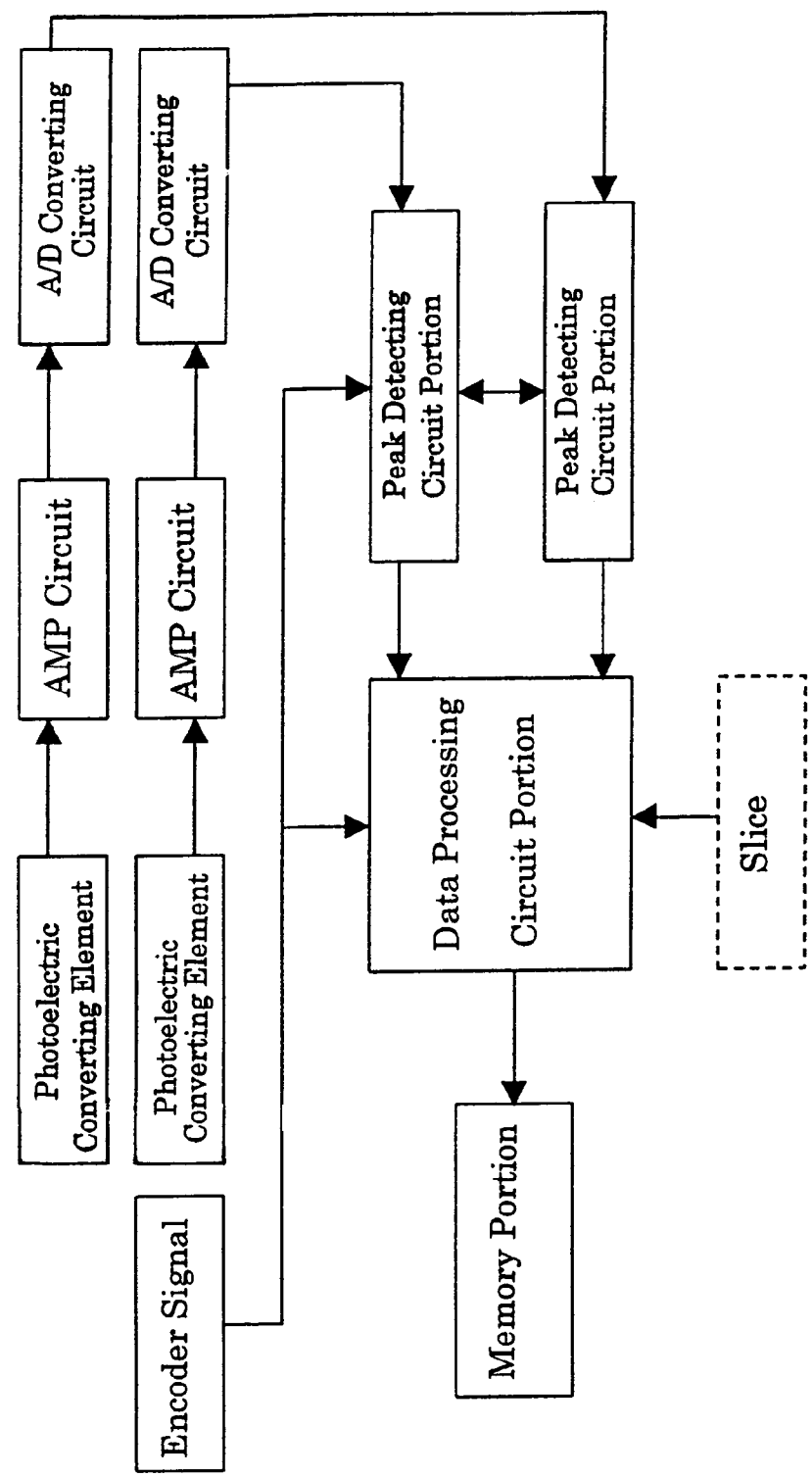
FIG. 2 is a block diagram showing a first embodiment of the invention.

FIG. 2 is a block diagram showing a preferred embodiment of the invention.

Referring to FIG. 2, two photoelectric converting elements are connected, by way of an AMP circuit and an A/D converting circuit in the order named, with their respective peak detecting circuit portions. These peak detecting circuit portions are connected to a data processing circuit portion. The data processing circuit portion is connected to a memory portion. An encoder signal is transmitted to the peak detecting circuit portion and the data processing circuit portion.

Figure 3:
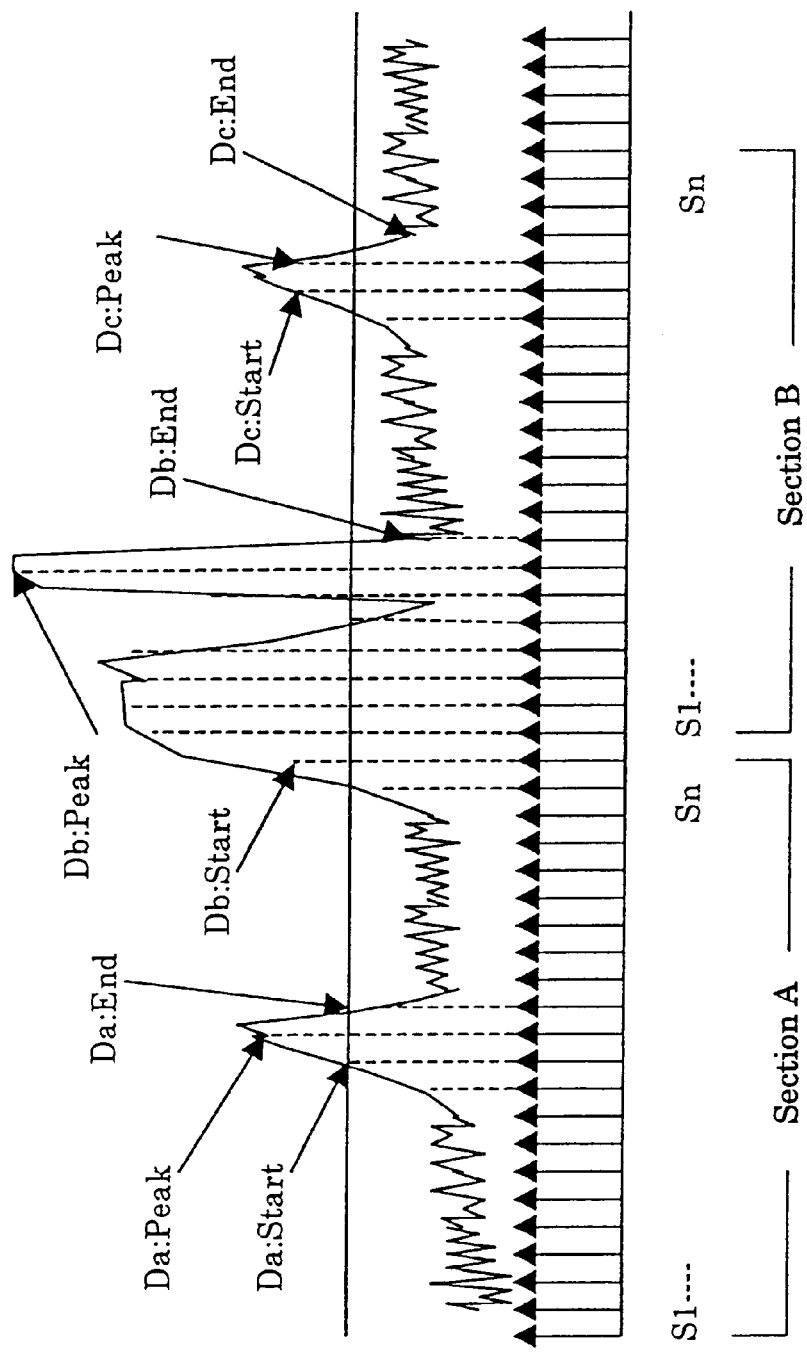
FIG. 3 is a diagram showing the processing manner according to the method of the embodiment shown in FIG. 2.

FIG. 3 shows a manner of processing according to the method of the invention.

In the method of the invention, when a scattered signal by a foreign matter exceeds a threshold signal (indicated by a horizontal solid line in FIG. 3) at a point while an inspecting beam is scanned in a predetermined direction, the point is stored as a start point (Start) and when, thereafter, the scattered signal by the foreign matter falls below the threshold signal at a point, the point is stored as an end point (End), and further, the point between the start point and the end point where the scattered signal by the foreign matter was at its maximum is stored as a peak (Peak). A foreign matter on the surface of the object of inspection is specified on the basis of positional information formed of the start point (Start), the peak (Peak), and the end point (End) as the positional data of the scattered signal by the foreign matter.

In FIG. 3, since foreign matters are specified by Da, Db, and Dc, the number of the foreign matters is found to be three. In this case, the data of the section A and the section B are not related to the number of foreign matters and, hence, the number of foreign matters is counted as three.

Figure 4:
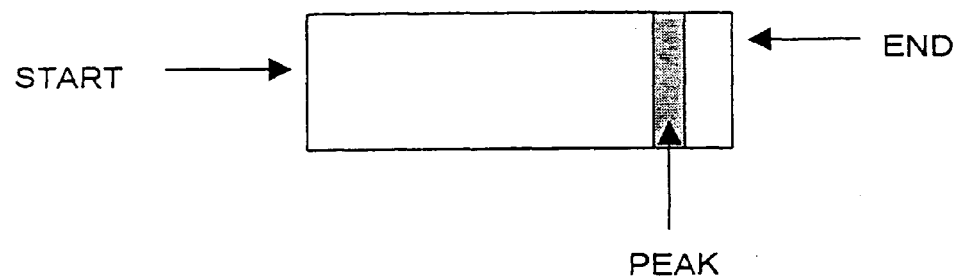
FIG. 4 is a conceptual drawing of determination of the existence of continuity in a foreign matter in the method of FIG. 3.

FIG. 4 is a conceptual drawing of judging a set of data as one foreign matter. Describing the foreign matter Db, in particular, the data of the foreign matter Db falls below the threshold signal (indicated by a horizontal solid line in FIG. 3) in the midway as shown in FIG. 4, but because the adjoining segment is near by, it is specified as one foreign matter.

Figure 5:
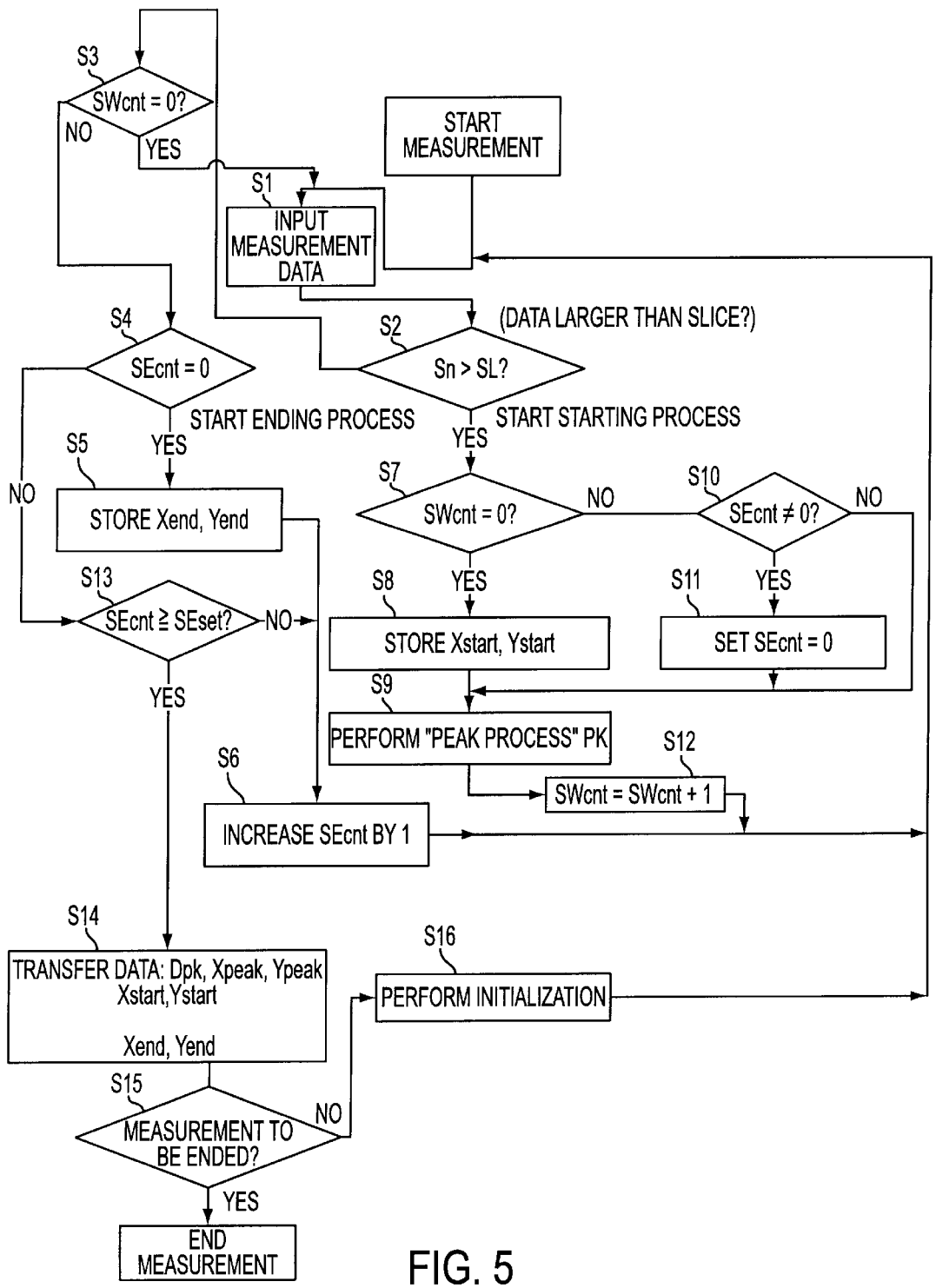
FIG. 5 is a flowchart of the method according to the first embodiment of the invention.

FIG. 5 shows an example of a flowchart of the method according to the invention.

In FIG. 5, when, first, the measurement is started, the measured data is input in step 1 and processing advances to step 2.

In step 2, it is determined whether or not the obtained measurement data Sn is greater than the slice level SL and, when it is smaller than that, processing advances to step 3, whereas, when it is greater than that, it advances to step 7.

In step 3, it is determined whether or not a width count SWcnt, which indicates the width of a foreign matter, is 0, i.e., whether or not the measurement data Sn has already exceeded the slice level SL. In other words, it is determined whether or not the data of a foreign matter was measured immediately before. Here "immediately before" means within the count of a predetermined value SEset, which is determined in step 13.

When the count SWcnt is 0, i.e., when there was no data of a foreign matter immediately before, processing returns to step 1 and, therein, processing of the next measured data is started. When the count SWcnt is not 0, i.e., when there was data of a foreign matter immediately before, processing advances to step 4 and, therein, such a process as to take a count SEcnt (count of non-signal period), i.e., to count the period during which the obtained measurement data Sn is smaller than the slice level SL, is performed.

When SEcnt=0 in step 4, it is determined whether or not an end signal count is 0, and when SEcnt=0, processing advances to step 5; otherwise, it advances to step 13.

In step 5, namely where the obtained measurement data Sn has lowered from the state of its being above the slice level SL to the state of its being below the slice level SL, the X and Y coordinates at this time are stored as Xend and Yend and processing advances to step 6. In step 6, the SEcnt value is increased by 1 and processing returns to step 1 and, therein, processing of the next measured data is started.

When it is determined in step 2 that the obtained measurement data Sn is greater than the slice level SL, processing advances to step 7. In step 7, it is determined whether or not the count of SWcnt is 0, i.e., it is determined whether the measurement data Sn has ever exceeded the slice level SL. When it has just exceeded it for the first time, processing advances to step 8. If it is not for the first time, processing advances to step 10.

In step 8, the coordinate values at this point are stored as the starting coordinates (the coordinates values of the start point) Xstart and Ystart of the foreign matter and then processing advances to step 9.

On the other hand, when it is determined in step 7 that the value of the count SWcnt from the start of a foreign matter is not 0, i.e., that it is not for the first time for the measurement data Sn to have exceeded the slice level SL, processing advances to step 10 and, therein, it is determined whether the count value of the non-signal period count SEcnt is not 0. When the non-signal period count SEcnt is not 0, the count value of the count SEcnt is reset to 0 in step 11 and processing advances to step 9. When the non-signal period count SEcnt is 0, processing directly advances to step 9.

In step 9, peak processing is made to determine whether or not the obtained measurement data at this time is greater than that obtained previously and store the greater of them as the peak data and processing advances to step 12.

In step 12, 1 is added to the value of the count SWcnt from the point of the starting coordinates of the foreign matter (the start point, corresponding to the front edge of the foreign matter) and, then, processing returns to step 1.

When SEcnt≠0, i.e, the count value of the non-signal period count SEcnt is not equal to 0 in step 4, processing advances to step 13. It is determined, therein, whether or not the non-signal period count SEcnt is greater than a preset value of the count SEset. When the non-signal period count SEcnt is smaller than the preset value of the count SEset, processing advances to step 6 for processing the next measured data.

On the other hand, when the non-signal period count SEcnt is greater than the preset value of the count SEset, processing advances to step 14.

In step 14, data of the coordinate values Xstart, Ystart of the start point of the foreign matter stored in step 8, the coordinate values Xend, Yend stored in step 5, and the peak value stored in the memory are transferred to be stored into memory as the coordinate values of the start point of the foreign matter under the current inspection, the coordinate values of the end point of the foreign matter, and the peak value and, then, processing advances to step 15.

In step 15, it is determined whether or not the measurement has been completed. When the measurement has been completed, the measurement is ended at this point. If not, processing advances to step 16.

In step 16, initialization is made, i.e., the start coordinate values Xstart. Ystart of the foreign matter, the end coordinate values Xend, Yend thereof, the peak value P, the non-signal period count SEcnt, and the count value SWcnt from the start of the foreign matter are reset to 0 and processing returns to step 1.

EMBODIMENT SHOWN IN FIG. 6, FIGS. 8–11

Figure 6:
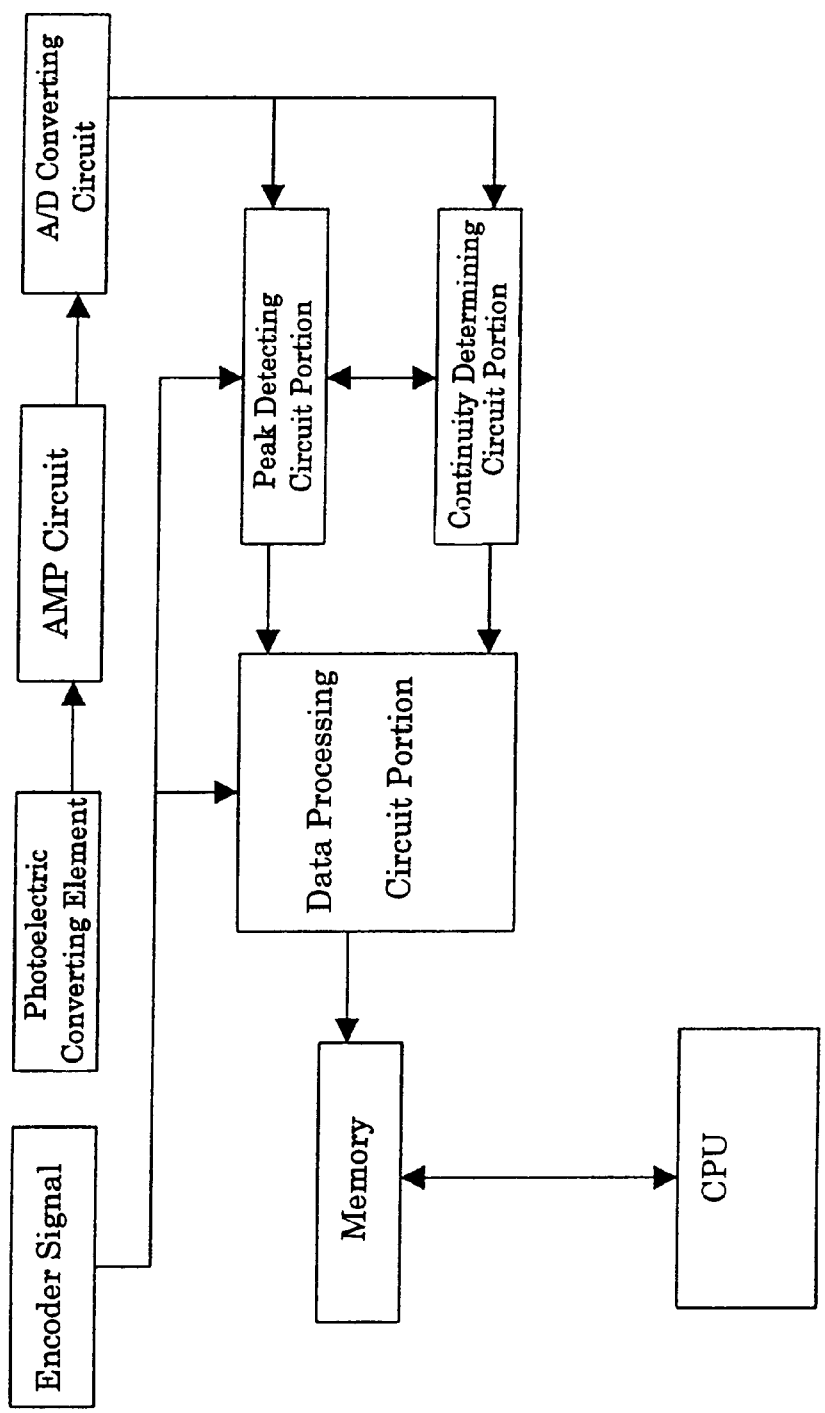
FIG. 6 is a block diagram showing a second embodiment of the invention.
Figure 7:
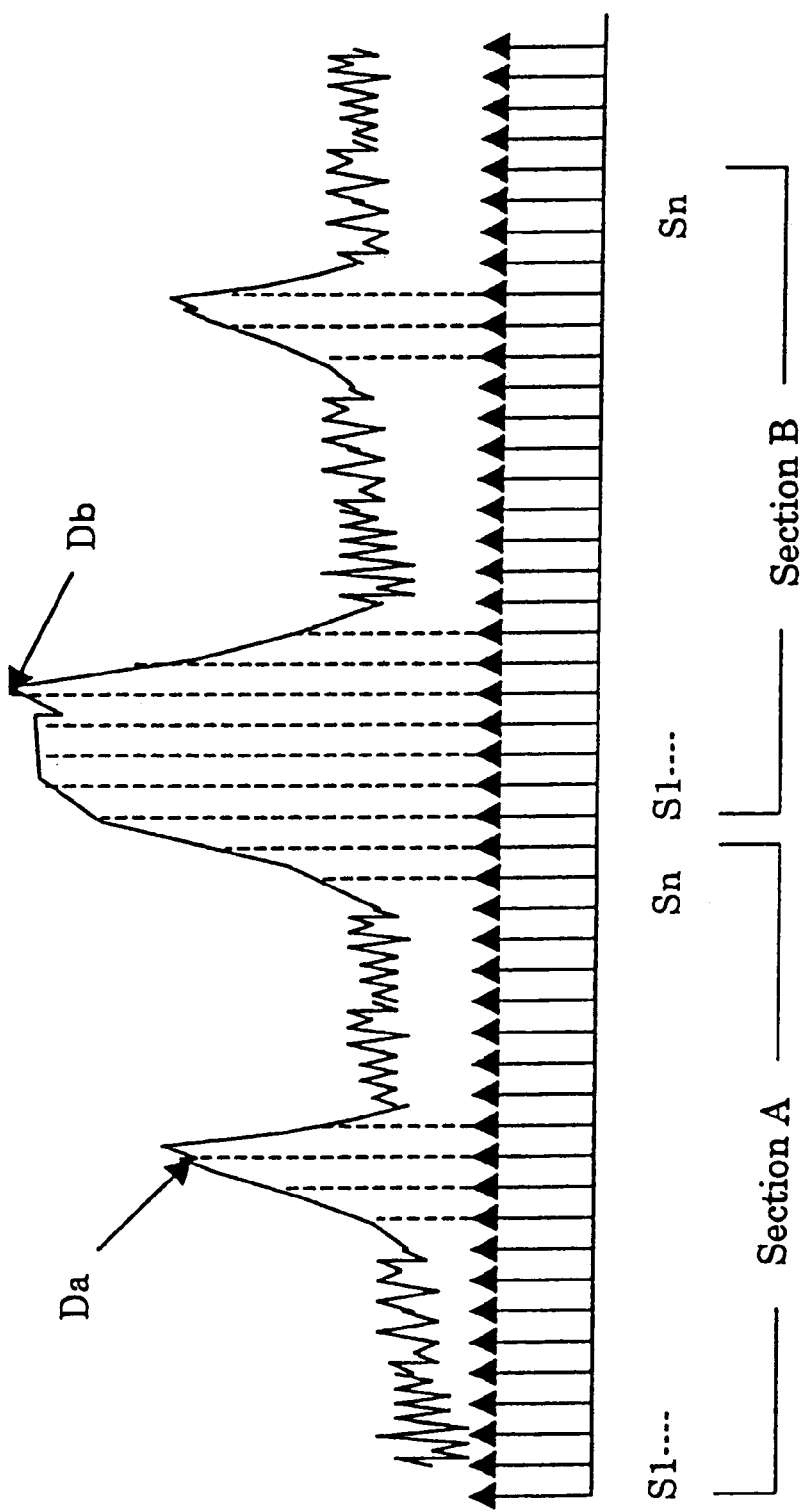
FIG. 7 is a diagram showing another prior art processing method on a pixel system.
Figure 8:
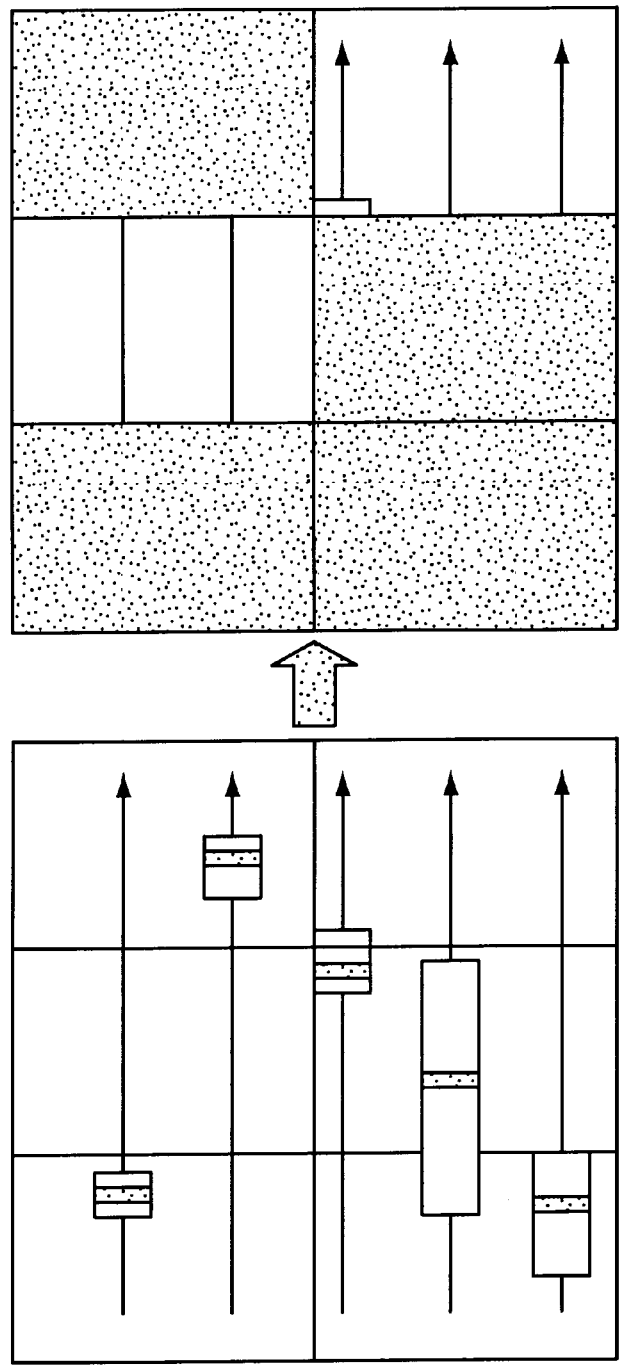
FIG. 8 is a diagram showing the manner of determining the existence of continuity in the direction of feed in the method of FIG. 7.

FIG. 6 is a block diagram showing a second embodiment of the invention.

Referring to FIG. 6, a photoelectric converting element is connected to a peak detecting circuit portion and a continuity determining circuit portion through an AMP circuit and an A/D converter circuit in the order named. The peak detecting circuit portion and the continuity determining circuit portion are connected to a data processing circuit portion. The data processing circuit portion is connected to a memory. An encoder signal is supplied to the peak detecting circuit portion and the data processing circuit portion. Further, a signal from the CPU is supplied to the memory.

Figure 9:
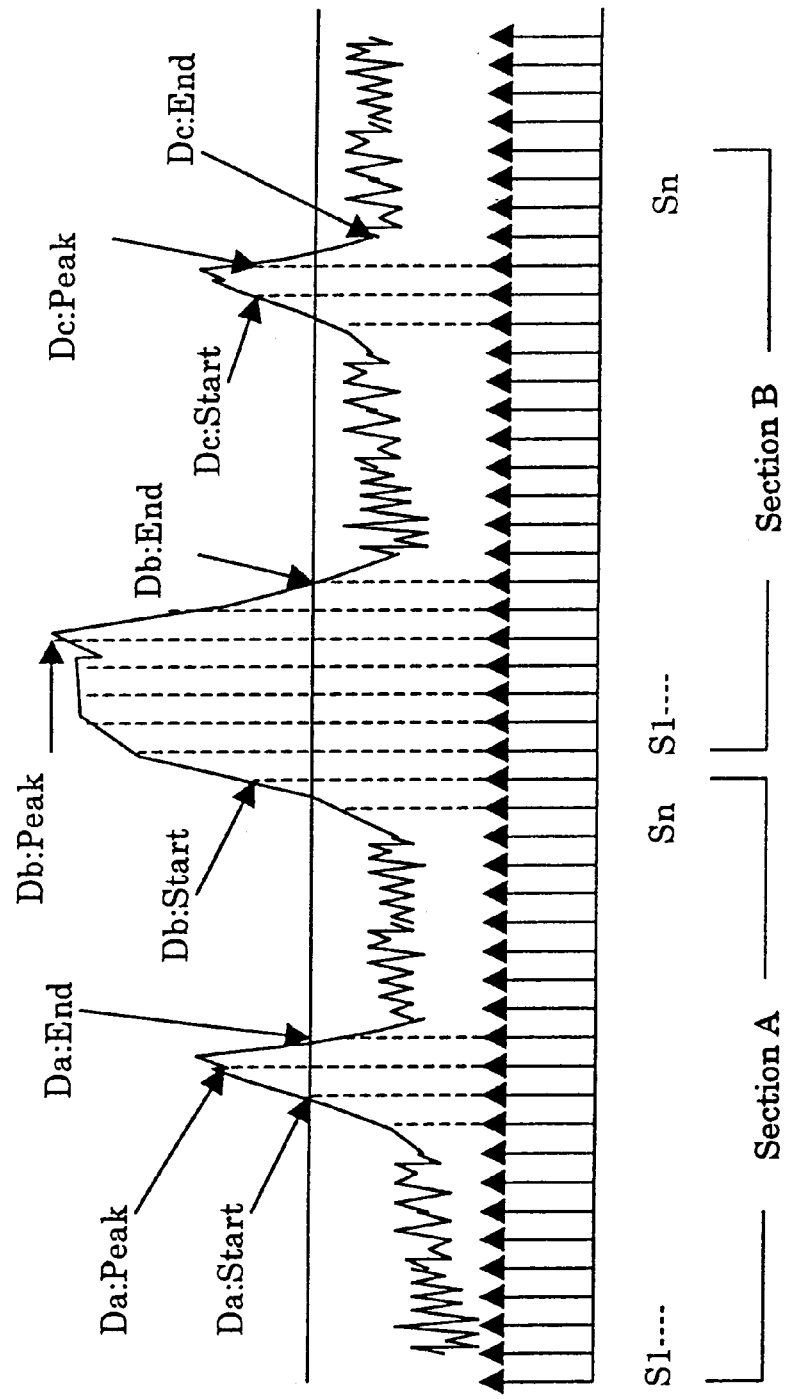
FIG. 9 is a diagram showing the manner of processing in the method of the first embodiment of the invention.

FIG. 9 shows a method of surface inspection according to the second embodiment of the invention.

In the state of inspection shown in FIG. 9, since the data in the sections are not related to the number of foreign matters, it is judged that there are three foreign matters Da, Db, and Dc.

This point will further be described below. While an inspecting light beam is scanned in a predetermined direction, when a foreign-matter scattered signal exceeds a threshold signal (indicated by a horizontal solid line in FIG. 9) at a point, the point is stored as a start point (Start) and, thereafter, when the foreign-matter scattered signal falls below the threshold signal at a point, the point is stored as an end point (End). Further the point between the start point and the end point where the foreign-matter scattered signal was at its maximum value is stored as a peak (Peak). A foreign matter on the surface of the object of inspection is specified on the basis of positional information, as the position data of the foreign-matter scattered signal, formed of the start point (Start), the peak (Peak), and the end point (End). In FIG. 9, foreign matters are specified by Da, Db, and Dc and the number of the foreign matters is three. In this case the data in the section A and the section B are not related to the number of foreign matters and, hence, the number of foreign matters is counted as three.

Figure 10:
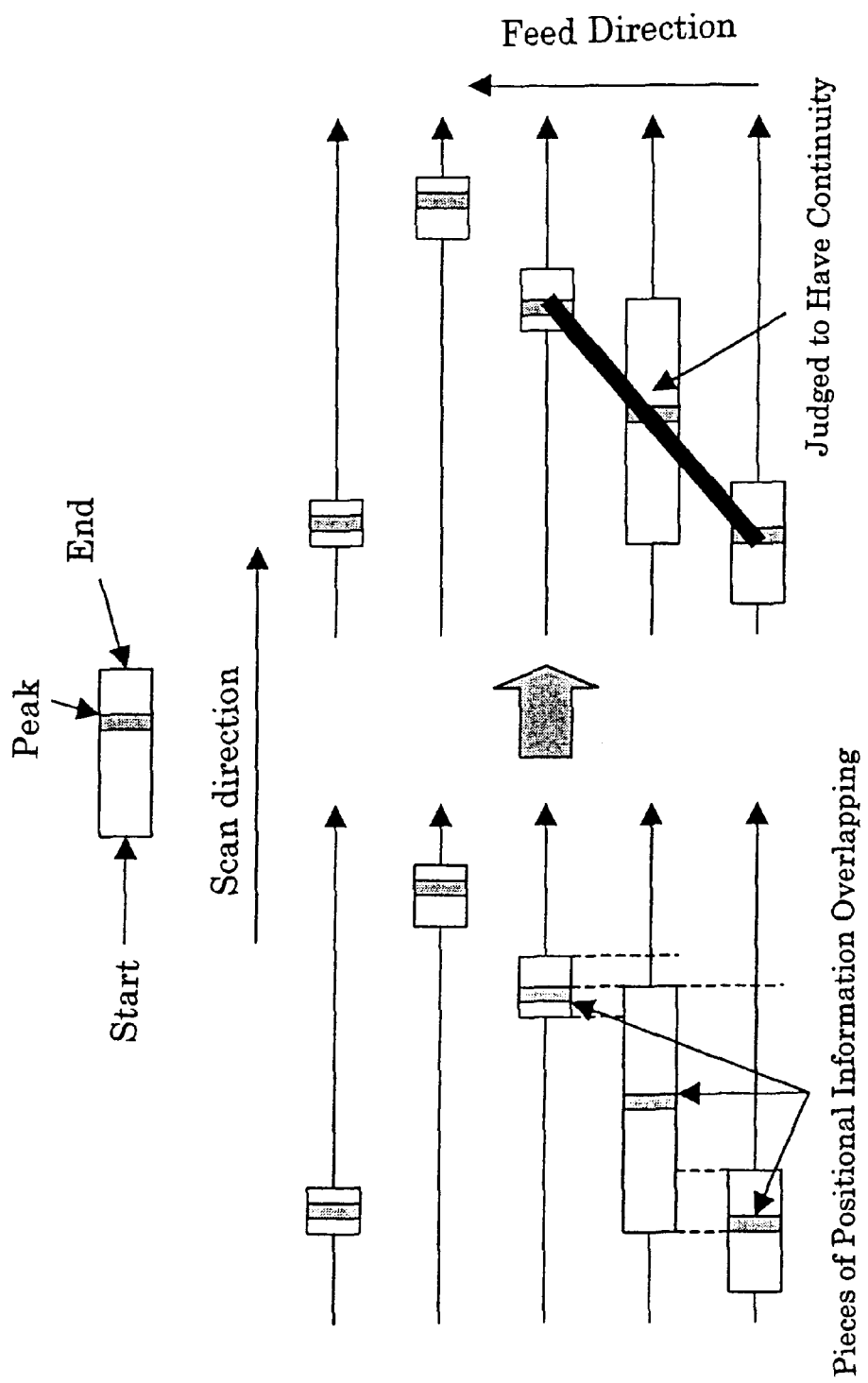
FIG. 10 is a diagram showing the manner of determining the existence of continuity in the direction of feed in the method of FIG. 9.

FIG. 10 is a conceptual diagram as to determination of the existence of continuity in a foreign matter.

In FIG. 10, the direction of the scan made by the inspecting light beam is formed of a combination of the direction in which the light beam is scanned and the direction in which the same is fed. When positional information of a start point and that of an end point of a set of data overlap each other in the direction of feed, it is determined that the foreign-matter scattered signals have continuity in the direction of feed. The signals from the start point to the end point are judged to represent a continuous foreign matter and the process to detect the peak data between the start point and the end point is constantly performed. At the point where a piece of data has fallen for the first time below the threshold signal, an end point is stored in memory and, at the same time, a sampling clock is started to count. If, then, the data has exceeded the threshold signal again within preset data, the earlier stored end point is cleared and the process for detecting the peak data is continued. Particularly, in processing the data, the following judgments are made as to the continuity.

(1) In the process concerning the continuity in the direction of scan, if the difference from the start point to the end point exceeds a predetermined value, the foreign matter is judged as a flaw; otherwise, it is judged as a dust.

(2) As to that in the direction of feed, it is determined whether positional information of the start point and that of the end point of the data overlap each other. If they are overlapping, it is judged that there is a continuity in the direction of feed. When the number of pieces of the data continuous in the direction of feed exceeds a predetermined number, the foreign matter is judged as a flaw; otherwise, it is judged as a dust.

In the case of FIG. 10, since the two pieces of positional information shown at the top of the drawing are not overlapping each other and hence not continuous, they are judged as two foreign matters. The three pieces of positional information at the bottom of the drawing are overlapping each other and hence continuous, and therefore they are judged to form one foreign matter.

Figure 11:
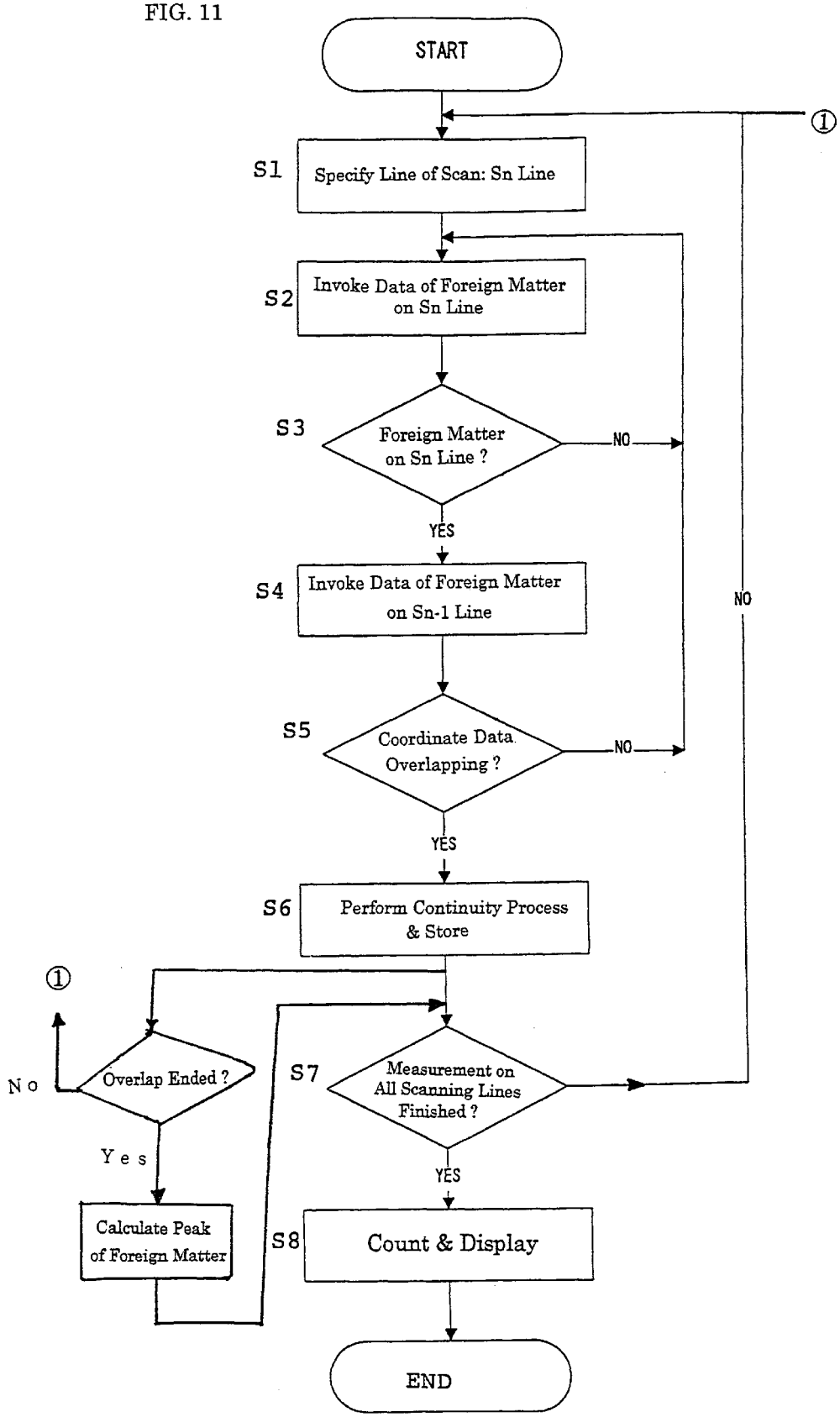
FIG. 11 shows an example of a flowchart of the method according to the first embodiment of the invention.

FIG. 11 shows an example of a flowchart of the method of the invention.

In FIG. 11, when a measurement; is started, a line of scan Sn is specified on the object of measurement in step 1 and processing advances to step 2. In step 2, the data on the line of scan Sn of the object of measurement is invoked and processing advances to step 3. In step 3, it is determined whether or not there is foreign matter data on the line of scan, i.e., whether or not there is included a signal exceeding the slice level SL. When there is foreign matter data, processing advances to step 4, and if there is no foreign matter data, processing returns to step 2 and the pertinent operations are repeated until foreign matter data is detected. In step 4 when foreign matter data is found on the line of scan Sn of the object of measurement, the foreign matter data on the preceding line of scan Sn-1 is invoked and then processing advances to step 5.

In step 5, it is determined whether or not there is an overlap between the foreign matter data on the current line of scan Sn of the object of measurement and the foreign matter data on the preceding line of scan Sn-1 of the object. If there is an overlap between them, processing advances to step 6 and, if there is no overlap, processing returns to step 2.

Here, an example where there is an overlap is such a state in which the stretch from the start coordinate to the end coordinate of a piece of foreign matter data in the scanning direction overlaps with that of another piece of foreign matter data. In step 6, the continuity process is performed and then processing advances to step 7.

When there is present an overlap between the foreign matter data on the current line of scan Sn of the object of measurement and the foreign matter data on the preceding line of scan Sn-1 of the object, it is judged that both the data are such that measure the same foreign matter and, in counting the number of the foreign matters, they are treated as one unit. Accordingly, the continuity process involves various processes to associate both the data with each other. For example, such processes are included therein as to treat the data between which continuity is judged present as one group, as to increment a correction value with 1 every time a continuity is found and subtract the correction value from the total number of the foreign matter signals on each of the lines of scan to thereby obtain the correct number of the foreign matters.

In step 7, it is determined whether or not measurement on all the lines of scan of the object of measurement is finished and, if it is not finished yet, processing returns to step 1 and measurement of the next line of scan Sn is performed.

On the other hand, between step 6 and step 7, it is determined whether or not the overlap is ended. When the answer is No, processing returns to the beginning step indicated by (1) and when the answer is Yes, the peak of the foreign matter is calculated and processing advances to step 7.

When measurement of all the lines of scan of the object of measurement is finished, such processes are performed in step 8 as to count the total number of foreign matters in which those foreign matters judged to have continuity between each other are counted as one unit and to display the foreign matters such that those judged to have continuity are distinguishable on a graphic display and, then, the measurement is ended.

The invention can be understood in more detail by referring to the specification and the drawings U.S. patent application Ser. No. 09/196,739 filed on Nov. 20, 1998, (now in condition for allowance) which claims priority to two Japanese Patent Applications, one of which is of Japanese Patent Application No. 9-336572, and particularly the surface inspecting apparatus shown in FIG. 12. The disclosure of the above-mentioned United States Patent Application is hereby incorporated by reference thereto.

What is claimed is:

1. An apparatus for surface inspection comprising:

a light source;

an irradiating optical system for directing an irradiating light beam from said light source onto a surface of an object under inspection;

a light receiving optical system for receiving a scattered light beam reflected from the surface of said object under inspection;

a photosensing portion for forming a surface data signal from the scattered light beam received by said light receiving optical system;

a displacement portion for continuously displacing a surface of said object under inspection, relative to said irradiating optical system and said light receiving optical system, in main and sub-scanning directions; and a foreign matter detecting portion for detecting foreign matter present on the surface of said object under inspection on a basis of a maximum value level of said surface data signal and measuring the position, in the sub-scanning direction, of the foreign matter present on the surface of said object under inspection on the basis of each levels of at least two adjoining surface data signals in the sub-scanning direction.

2. An apparatus for surface inspection according to claim 1, wherein said foreign matter detecting portion measures the position of the foreign matter present on the surface of the object under inspection on a basis of each peak levels of at least two adjoining surface data signals in the sub-scanning direction.

3. An apparatus for surface inspection according to claim 2, wherein said foreign matter detecting portion measures the position, in the main scanning direction and the sub-scanning direction, of the foreign matter present on the surface of said object under inspection on the basis of at least two adjoining surface data signals in the sub-scanning direction given that an intensity distribution of the irradiating light beam is in conformity with a specific curve.

4. An apparatus for surface inspection according to claim 3, wherein said foreign matter detecting portion measures the position, in the sub-scanning direction of the foreign matter present on the surface of said object under inspection on the basis of at least two adjoining surface data signals in the sub-scanning direction given that the intensity distribution of the irradiating light beam of the irradiating optical system is in conformity with a Gaussian curve, according to the numerical expression as mentioned below:

$$x = \{D^2/8\}\ln(\ln/\ln + 1) - p^2\}/2p$$

where x; is the position, in the sub-scanning direction, of the foreign matter present on the surface of said object under inspection D: beam diameter p: scanning pitch n: the scanning number of the beam In: the peak level of the n-the received-light signal In+1: the peak level of the (n+1)-the received-light signal.

5. An apparatus for surface inspection according to claim 1, wherein said foreign matter detecting portion measures the position, in the main scanning direction and the sub-scanning direction, of a center of the foreign matter present on the surface of said object under inspection on the basis of positional data of each of at least two adjoining surface data signals in the sub-scanning direction.

6. An apparatus for surface inspection according to claim 5, wherein said foreign matter detecting portion is measures the position, in the main scanning direction and the sub-scanning direction, of the foreign matter present on the surface of said object under inspection by measuring the position of a center of gravity of said object under inspection from starting and ending positions of at least two adjoining surface data signals in the sub-scanning direction.

7. An apparatus for surface inspection according to claim 1, wherein said foreign matter detecting portion is measures the position, in the main scanning direction and the sub-scanning direction of a center of the foreign matter present on the surface of said object under inspection on the basis of an area in the surface data signal in the main scanning direction.

8. An apparatus for surface inspection according to claim 7, wherein said foreign matter detecting portion is measures a sectional area produced by the foreign matter from a change in the surface data signal in the main scanning direction of adjoining surface data signals and to measure the position, in the main scanning direction and the subsscanning direction, of a center of the foreign matter present on the surface of said object under inspection, on the basis of the obtained sectional area.

9. An apparatus for surface inspection comprising:

a light source;

an irradiating optical system for throwing an irradiating light beam from said light source onto the source of an object under inspection;

a light receiving optical system for receiving a scattered light beam reflected from the surface of said object under inspection irradiated by the irradiating optical system;

a photosensing portion for forming a surface data signal from the scattered light beam received by said light receiving optical system;

a displacement portion for displacing the surface of said object under inspection, relative to said irradiating optical system and said light receiving optical system, continuously in a main scanning direction and intermittently in a sub-scanning direction; and a foreign matter detecting portion for detecting a foreign matter present on the surface of said object under inspection on the basis of a maximum value level of said surface data signal and measuring the position, in the sub-scanning direction, of the foreign matter present on the surface of said object under inspection on the basis of each levels of at least two adjoining surface data signals in the sub-scanning direction on the presumption that an intensity distribution of the irradiating light beam of the irradiating optical system is in conformity with a specific curve.

10. An apparatus for surface inspection according to claim 9, wherein said foreign matter detecting portion is designed to measure the position, in the sub-scanning direction, of the foreign matter present on the surface of said object under inspection on the basis of at least two adjoining surface data signals in the sub-scanning direction on the presumption that the intensity distribution of the irradiating light beam of the irradiating optical system is in conformity with a Gaussian curve, according to the numerical expression as mentioned below:

$$x + \{D^2/8)\ln(In/In+1) - p^2\}/2p$$

where x: position, in the sub-scanning direction, of the foreign matter present on the surface of said object under inspection D: beam diameter p: scanning pitch n: the scanning number of the beam In: the peak level of the n-th received-light signal In+1: the peak level of the (n+1)-th received-light signal.

* * * * *